United States Patent

Armand et al.

[11] Patent Number: 6,120,696
[45] Date of Patent: Sep. 19, 2000

[54] PROTON CONDUCTORS IN LIQUID FORM

[75] Inventors: Michel Armand, Montréal, Canada;
Christophe Michot, Grenoble, France;
Bruno Kapfer, Longueuil, Canada

[73] Assignees: Centre National de la Recherche Scientifique, Paris, France;
Hydro-Quebec, Montreal, Canada

[21] Appl. No.: 09/125,792

[22] PCT Filed: Dec. 30, 1997

[86] PCT No.: PCT/CA97/01012

§ 371 Date: Aug. 28, 1998

§ 102(e) Date: Aug. 28, 1998

[87] PCT Pub. No.: WO98/29877

PCT Pub. Date: Jul. 9, 1998

[30] Foreign Application Priority Data

Dec. 30, 1996 [CA] Canada ................................. 2194127
Mar. 5, 1997 [CA] Canada ................................. 2199231

[51] Int. Cl.[7] ................................. H01B 1/12; B02F 1/15
[52] U.S. Cl. ................................. 252/62.2; 359/265; 359/270
[58] Field of Search ................................. 252/62.2; 359/265, 359/270

[56] References Cited

U.S. PATENT DOCUMENTS 5,688,613  11/1997  Li et al. ................................. 429/192
5,795,496  8/1998  Yen et al. ................................. 252/62.2

*Primary Examiner*—Georgia Epps
*Assistant Examiner*—Margaret Burke
*Attorney, Agent, or Firm*—Oblon, Spivak, McClelland, Maier & Neustadt, P.C.

[57] ABSTRACT

The invention is a proton conductor in liquid form, comprising a mixture of the following components: (a) an acid addition salt of a nitrogen base, having the formula:

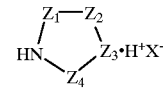

wherein:

$Z_1$, $Z_2$, $Z_3$ and $Z_4$, identical or different, each represent a group $-N=$ or $-C(Y_i)=$ in which $Y_i$ represents a hydrogen atom, a linear or branched alkyl group having 1 to 20 carbon atoms, a fluoroalkyl radical having 1 to 20 carbon atoms, or an oxoalkyl or azaalkyl radical having 1 to 20 carbon atoms, with the proviso that at least one and at most two of the groups $Z_1$, $Z_2$, $Z_3$ and $Z_4$ represents $-N=$, two adjacent carbon atoms being optionally hydrogenated and the nitrogen base optionally being part of a polymeric network, and $X^-$ represents an anion derived from an acid selected from the group consisting of sulfonic acids of formula $R_FSO_3H$, sulfonimides of formula $(R_FSO_2)(R'_FSO_2)NH$ and methylides of formula $(R_FSO_2)(R'_FSO_2)CH_2$ or $(R_FS_2)(R'_FSO_2)(R''_FSO_2)CH$, in which $R_F$, $R'_F$ and $R''_F$ each represents a radical $F(CF_2)_n-$, n being comprised between 0 and 6, the acid optionally being part of a polymeric network; and (b) a nitrogen base having the formula:

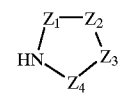

in which $Z_1$, $Z_2$, $Z_3$ and $Z_4$ have the aforesaid meanings, the nitrogen base optionally being part of a polymeric network; components (a) and (b) being present in proportions to form a composition having a melting point lower than 25° C. The proton conductor is useful as an electrolyte in various electrochemical systems.

34 Claims, 5 Drawing Sheets

PROTON CONDUCTORS IN LIQUID FORM

FIELD OF THE INVENTION

The present invention relates to novel proton conductors in liquid form and to their use as liquid, gel or polymer electrolytes in various electrochemical systems.

BACKGROUND OF THE INVENTION

The most common proton conductors are obtained by doping water with an acid such as HCl or $H_2SO_4$, or a base such as KOH or $NH_3$. Thus, aqueous solutions of sulfuric acid have a high proton conductivity greater than $10^{-2}$ S·cm$^{-1}$ and solutions of potassium hydroxide which are also very conducting are widely used as electrolytes in Nickel-Cadmium.

Proton conductors requiring the presence of water in order to function generally have a field of use limited in temperature due to the evaporation of the water and a field of redox stability limited to that of water. The presence of water also usually induces corrosion phenomena within the systems utilizing these electrolytes.

In order to overcome these redhibitory problems with respect to certain applications, a number of works have born on the study of anhydrous proton conductors. From the various classes of materials resulting from these researches, there have been more particularly obtained anhydrous proton conductors by substituting the aqueous solvent with non-hydroxylic solvating polymers such as polyethylene oxide, polyvinylpyrrolidone, polyethyleneimine or polyaminopropylsiloxane.

By doping these polymers with acids or bases, one obtains anhydrous proton conductors. For examples, dissolving orthophosphoric acid $H_3PO_4$ in polyethylene oxide (POE) enables one to obtain an acidic proton conductor, and dissolving sulfonamide $H_2NSO_2NH_2$ in the same polymer enables one to obtain a basic proton conductor.

These electrolytes are useful for making electrochemical systems, particularly light-modulating systems, but they still have major drawbacks. Proton conductors obtained by dissolving $H_3PO_4$ in POE are corrosive due to the high acidity of the medium ($pK_a \approx 0$). On the contrary, the high basicity ($pK_a \approx 11-12$) of proton conductors obtained by dissolving sulfonamides in POE limits their uses. Indeed, in the presence of many electrode materials containing metallic species, there is formed a passivation layer which is a poor conductor of metallic cations complexed with sulfamide. On the other hand, these electrolytes are poor conductors at low temperature.

SUMMARY OF THE INVENTION

In order to overcome the above drawbacks, the inventors have found quite surprisingly that binary mixtures of certain nitrogen bases belonging to the azole family with appropriate acid addition salt of these nitrogen bases form proton conductors having a melting point lower than room temperature, a weak vapor tension and a conductivity similar to that obtained in aqueous medium.

According to the present invention, there is thus provided a proton conductor in liquid form, comprising a mixture of the following components (a) and (b):

a) an acid additive salt of a nitrogen base, having the formula:

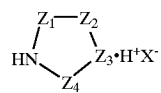

wherein:
$Z_1$, $Z_2$, $Z_3$ et $Z_4$, identical or different, each represent a group —N= or —C($Y_i$)= in which $Y_i$ represents a hydrogen atom, a linear or branched alkyl group having 1 to 20 carbon atoms, a fluoroalkyl radical having 1 to 20 carbon atoms, or an oxoalkyl or azaalkyl radical having 1 to 20 carbon atoms, with the proviso that at least one and at most two of the groups $Z_1$, $Z_2$, $Z_3$ et $Z_4$ represents —N=, two adjacent carbon atoms being optionally hydrogenated and the nitrogen base optionally being part of a polymeric network, and X$^-$ represents an anion derived from an acid selected from the group consisting of sulfonic acids of formula $R_FSO_3H$, sulfonamides of formula $(R_FSO_2)(R'_FSO_2)NH$ and methylides of formula $(R_FSO_2)(R'_FSO_2)CH_2$ or $(R_FSO_2)(R'_FSO_2)(R''_FSO_2)CH$, in which $R_F$, $R'_F$ and $R''_F$ each represents a radical $F(CF_2)_n$—, n being comprised between 0 and 6, the acid optionally being part of a polymeric network; and b) a nitrogen base having the formula:

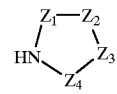

in which $Z_1$, $Z_2$, $Z_3$ and $Z_4$ have the aforesaid meanings, the nitrogen base optionally being part of a polymeric network;

components (a) and (b) being present in proportions to form a composition having a melting point lower than 25° C.

The invention also relates to a liquid electrolyte consisting of a proton conductor as defined above.

The invention is also directed to a polymer electrolyte comprising a proton conductor as defined above, dissolved in a polymer comprising at least on polar group.

Preferably, the composition comprising the mixture of components (a) and (b) is substantially eutectic.

Examples of nitrogen bases include the azoles of formula:

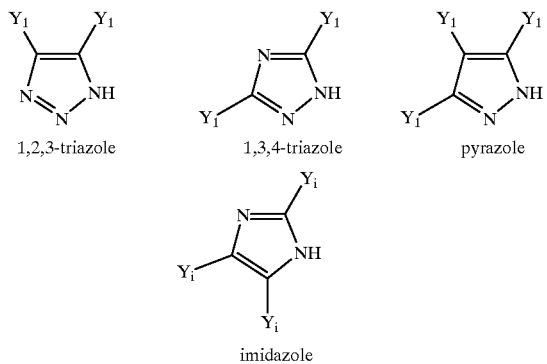

1,2,3-triazole     1,3,4-triazole     pyrazole imidazole wherein $Y_i$ has the aforesaid meaning.

Use can also be made of partially hydrogenated azoles such as the imidazolines of formula:

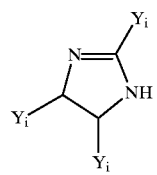

wherein $Y_i$ has the aforesaid meaning.

The selection of the nitrogen base enables one to control the pH of the proton conductors according to the invention. Thus, the binary mixtures triazole/triazolium have a $pK_a$ of the order of 2, the binary mixtures imidazole/imidazolium have a $pK_a$ of the order of 7 and the binary mixtures imidazoline/imidazolinium have a $pK_a$ of the order of 10.

Examples of acids include triflic acid, bisfluorosulfonimide, bistrifluoromethanesulfonimide, bistrifluoromethanesulfonylmethane, tristrifluoromethanesulfonylmethane and trisfluorosulfonylmethane.

The binary mixtures comprising the above components (a) and (b) are anhydrous proton conductors. Indeed, a nitrogen base which is protonated is capable of transferring its proton to a non-protonated nitrogen base according to a Grotthus mechanism, permitting the displacement of the proton in these media. For example, in the case of the binary mixture imidazole/imidazolium triflate having an eutectic composition (3:1 molar), the conductivity of this mixture is greater than $10^{-3}$ $\Omega^{-1}$·$cm^{-1}$ at 25° C. Such a mixture thus constitutes a neutral anhydrous proton conductor having a high conductivity.

The proton conductors according to the invention are particularly interesting for light-modulating systems called electrochrome. Electrochrome systems generally utilize films of wide band gap semi-conducting materials such as $HWO_3$ or $IrO_2H_x$, $H_xTiO_2$, $H_xTa_2O_5$, $H_xMnO_2$, $H_xCO_2$, $H_xNiO_2$, x being typically comprised between 0 and 0.4, in which the concomitant injection of extraction of protons and electrons results in a variation of the optical absorption or reflectance in the visible or infrared spectrum.

Other electrochrome systems utilize soluble precursors of highly colored free radicals such as viologens ("Weitz blue"), the coloration of which is obtained by reduction, or 1,4-tetraalkyl aryl-diamines ("Wurster blue"), the coloration of which is obtained by oxidation. However, these compounds when in the colored state have only a limited stability, particularly with respect to light and oxygen, and cannot be utilized in windowpanes or display systems which are exposed to natural light.

The proton conductors according to the invention rely on a new principal of reversible formation of colored species, by electrochemical reactions involving the injection of two electrons and one or two protons, as follows:

[ox]$^+$+2e$^-$+H$^+$→[red]

[ox]$^-$+2e$^-$+2H$^+$→[red]$^-$

[ox]+2e$^-$+2H$^+$→[red]

wherein passing from ox to red corresponds to a change of color. In this case, the colored species are not radicals and have a stability which is markedly improved over radical systems. The proton conductors according to the invention not only have a high protonation power and a pH controlled by the selection of the azole-type heteroatom, but also a much wider operating temperature range and a solubilizing power towards organic molecules, with respect to aqueous media.

The present invention therefore also provides an electrochrome system comprising two transparent semi-conducting electrodes arranged in spaced-apart opposed relationship to one another, each electrode being fixed on one side thereof to a transparent support and comprising on an other side thereof a coating of a wide band gap semi-conducting material, and a polymer electrolyte as defined above, disposed between the electrodes and contacting the coatings of semi-conducting material.

The invention is also directed to an electrochrome system comprising two transparent semi-conducting electrodes arranged in spaced-apart opposed relationship to one another, each electrode being fixed on one side thereof to a transparent support, and a polymer electrode as defined above, disposed between the electrodes and contacting the other side of each electrode, the polymer electrolyte comprising at least one redox coloring agent added thereto.

According to the invention, there is also provided an electrochrome system comprising two transparent semi-conducting electrodes arranged in spaced-apart opposed relationship to one another, each electrode being fixed on one side thereof to a transparent support and one of the electrodes comprising on the other side thereof a coating of a wide band gap semi-conducting material, and a polymer electrolyte as defined above disposed between the electrodes and contacting the coating of semi-conducting material. The polymer electrolyte comprises at least one redox couple added thereto, the redox couple being complementary to the wide band gap semi-conducting material.

Non-limiting examples of molecules capable of undergoing reversible color changes include the following:

| reduced form | oxidized form |
| --- | --- |

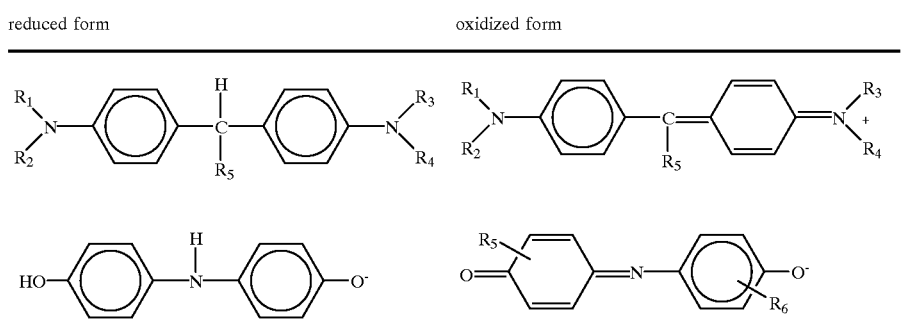

| reduced form | oxidized form |
|---|---|

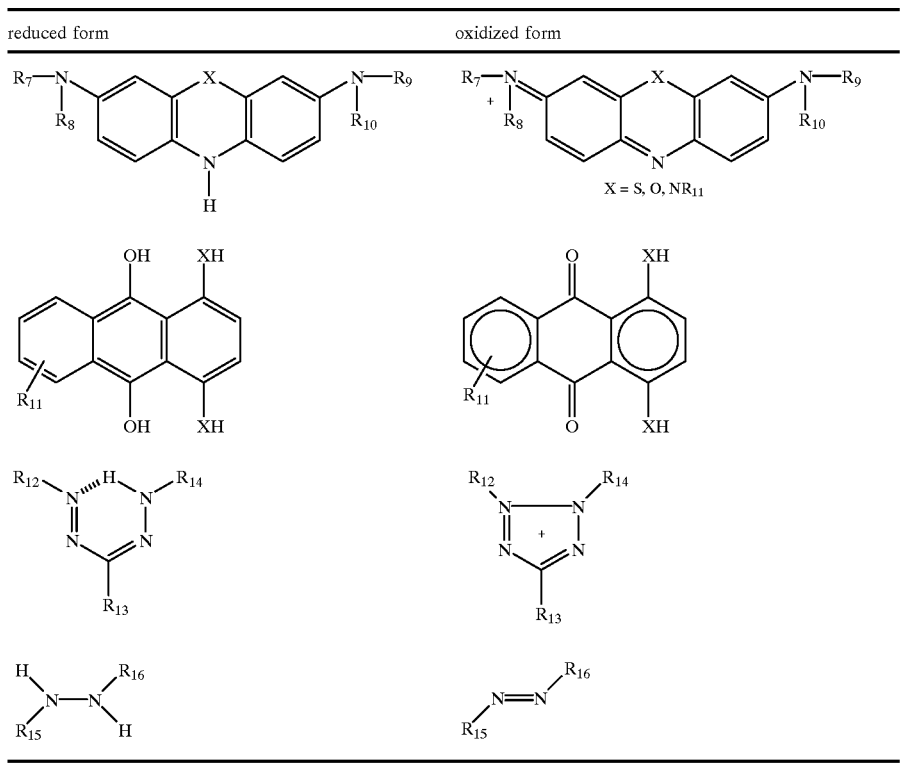

In the above formulas, $R_1$ to $R_{10}$ are alkyl, aryl, arylalkyl or alkylaryl groups optionally containing oxa, aza, thia substituents or halogens, nitro, cyano, carboxylate, sulfonate, onium groups, in the alkyl chains or in the rings.

$R_{11}$ to $R_{16}$ are aryl, alkylaryl, heterocycle groups optionally containing oxa, aza, thia substituents or halogens, nitro, cyano, carboxylate, sulfonate, onium groups, in the alkyl chains or in the rings.

Examples of coloring agents or redox couples providing a color change by the application of current include:

leuco(violet crystal) ←→ crystal violet (violet oxidized form), leuco(malachite green) ←→ malachite green (green oxidized form), leuco(methylene blue) ←→ methylene blue (blue oxidized form), bis(4-hydroxyphenylamine) ←→ imidazolium salt of indophenol (red oxidized form), 3,4-dihydroxy-9,10-anthraquinone (alizarine, red reduced form) ←→ 3,4,9,10-tetrahydroxy-anthracene, 4,4'bis(4-nitrophenylformazan)-3, 3'-methoxy-biphenyl (blue reduced form) ←→ tetranitrotetrazolium blue cation, triphenyl formazan (blue reduced form) ←→ 2,3,5 triphenyl-2H-tetrazolium cation, 1,4-diaminophenyl-hydrazino-1-naphthalene ←→ 1,4-diaminophenyl-azo-1-naphthalene (Fat brown RR, chestnut oxidized form).

The redox couples can be associated in a complementary manner, that is, one of the reagents undergoes a color change by reduction whereas its complement undergoes a color change by oxidation. It is thus possible to incorporate into the medium molecules undergoing redox reactions without a color change, thereby enabling the reaction of formation of the coloring agent to be effected at a single electrode. For example, compounds involving the formation and cleavage of disulfide bonds such as dimercaptothiadiazole, mercaptomethyltetrazole, the corresponding anions of which are stables in the electrolyte of the invention, can be cited.

It is also possible to associate with the above families of coloring agents organometallic molecules exhibiting stable redox couples such as ferrocene or its derivatives, or to use counter-electrodes on which a wide band gap semiconducting material such as $H_xWO_3$, $IrO_2H_x$, $H_xTiO_2$, $H_xTa_2O_5$, $H_xMnO_2$, $H_xNiO_2$, $H_xCoO_2$ (x being typically comprises between 0 and 0,4), is deposited.

The proton conductors according to the invention are also interesting for electrochemical generators, electrochemical supercapacitors comprising at least one carbon electrode, at least one metallic oxide electrode or at least one polymer having redox properties. The proton conductors according to the invention can be used as anhydrous protic solvents having a high solvating power and also has solvents for effecting chemical, photochemical or electrochemical reactions.

In addition to all the advantages mentioned above, the proton conductors according to the present invention form polymer electrolytes when they are mixed with polymers containing polar groups, such as polyethers, polyesters, polyethyleneimine, polyacrylonitrile, vinylidene polyfluoride, or polyvinyl butyrale. Membranes having both a good mechanical properties and a high conductivity are thus obtained. Moreover, the conductivity of the liquid, gel or polymer proton conductors according to the present invention can be increased by adding at least one polar solvent which is hardly volatile, such dimethylformamide, dimethylacetamide, tetraalkyl-sulfamides or glymes.

BRIEF DESCRIPTION OF THE DRAWINGS

Further features and advantages of the invention will become more clearly apparent from the following description of preferred embodiments, with reference to the accompanying drawings, in which.

DESCRIPTION OF PREFERRED EMBODIMENTS

Figure 1:
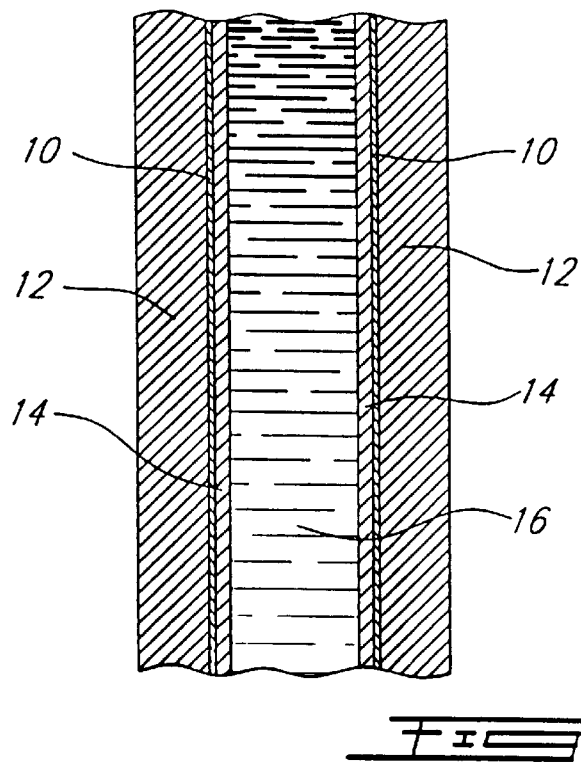
FIG. 1 is a partial schematic sectional view of an electrochrome system comprising a polymer electrolyte according to the invention.
Figure 2:
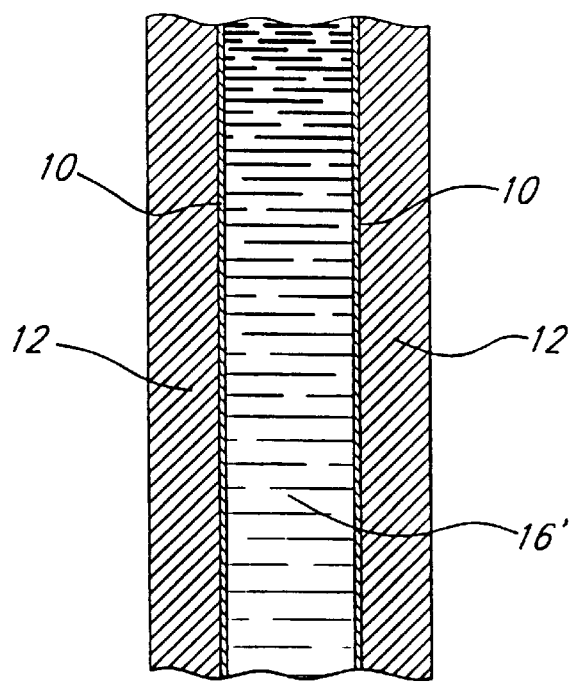
FIG. 2 is a partial schematic sectional view of another electrochrome system comprising a polymer electrolyte according to the invention.

The electrochrome system illustrated in FIG. 1 comprises two transparent semi-conducting electrodes 10 arranged in spaced-apart opposed relationship to one another, each electrode 10 being fixed on one side thereof to a transparent support 12 such as glass and comprising on the other side thereof a coating 14 of a wide band gap semi-conducting material. A polymer electrolyte 16' according to the invention is disposed between the electrodes 10 and contacts the coatings 14 of semi-conducting material. The electrochrome system illustrated in FIG. 2 is similar to the one shown in FIG. 1, with the exception that the electrodes 10 are not provided with a coating 14, the polymer electrolyte 16' comprising instead two complementary redox coloring agents added thereto. The application of a voltage to electrodes 10 results in a color change of the coatings 14 in the case of the electrochrome system shown in FIG. 1 and a color change of the redox coloring agents present in the polymer proton electrolyte 16' in the case of the electrochrome system shown in FIG. 2.

Figure 3:
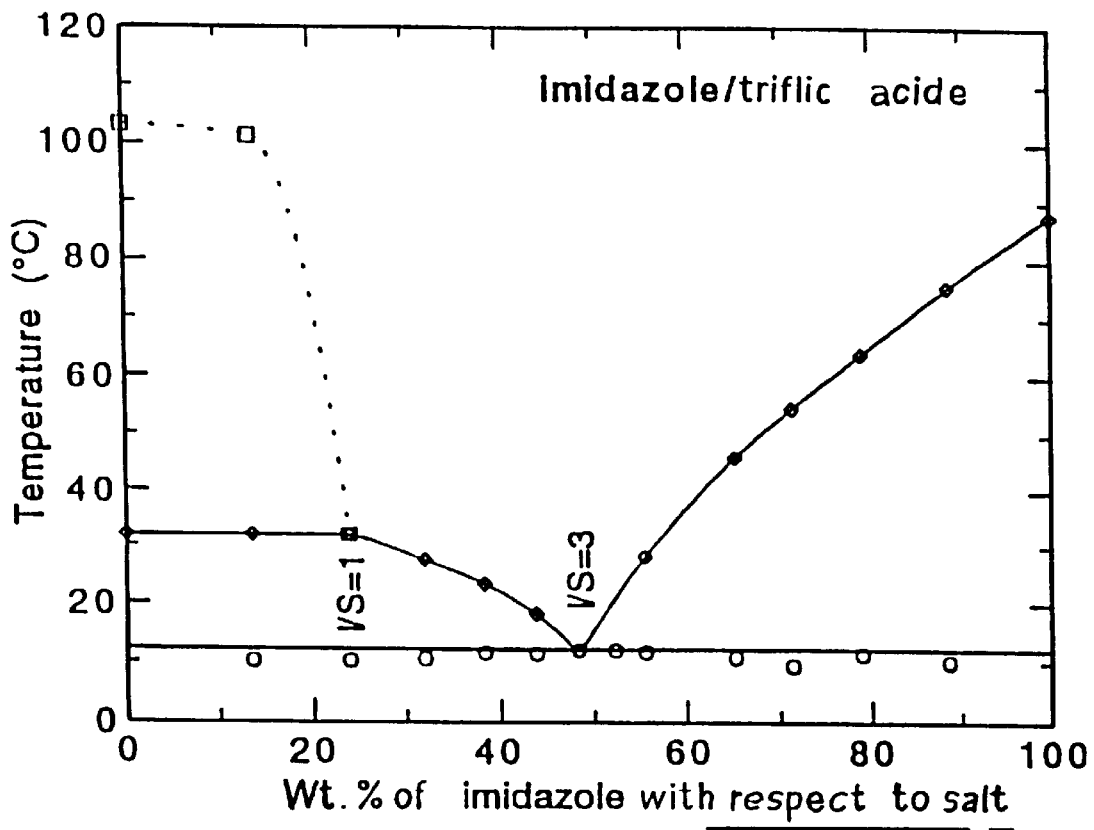
FIG. 3 represents the phase diagram of the binary mixture imidazole/imidazolium triflate.
Figure 4:
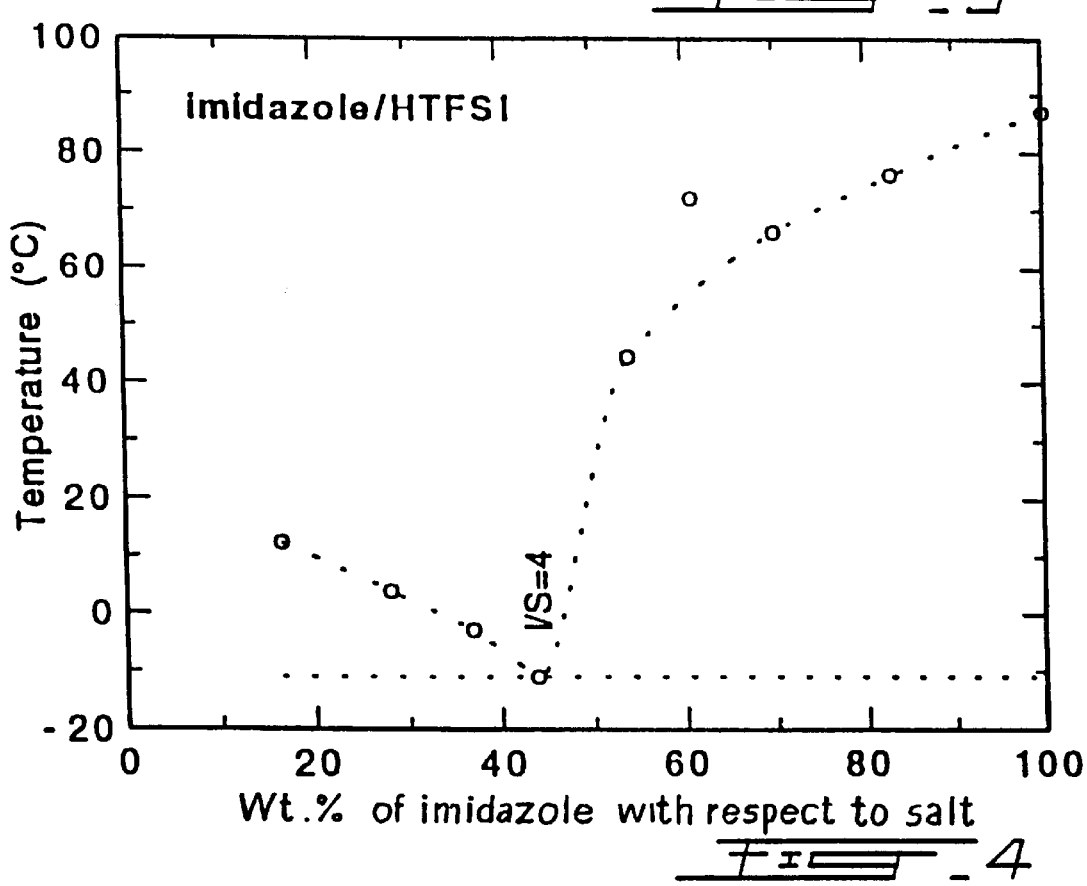
FIG. 4 represents the phase diagram of the binary mixture imidazole/imidazolium bis (trifluoromethane-sulfonimide)

FIG. 3 represents the diagram of the binary mixture imidazole/imidazolium triflate. As shown, this binary mixture has an eutectic plateau for a molar ratio imidazole/salt (I/S) equal to 3, with a melting point of about 12° C. FIG. 4, on the other hand, represents the phase diagram of the binary mixture imidazole/imidazolium bistrifluoromethane-sulfonimide. As shown in FIG. 4, this binary mixture has an eutectic plateau for a molar ratio I/S equal to 4, with a melting point of about −10° C. Generally, the binary mixture imidazole/imidazolium bisfluorosulfonimide at its eutectic composition (molar ratio I/S equal to 4) has a melting point lower than −20° C. The nature of the substituents has also an influence on the properties of the liquid conductors; thus, in the case of the binary mixture 2-hexylimidazole/2-hexylimidazolium triflate, the temperature of the eutectic plateau for a molar ratio I/S equal to 3 or 4 is lower than −10° C.

Figure 5:
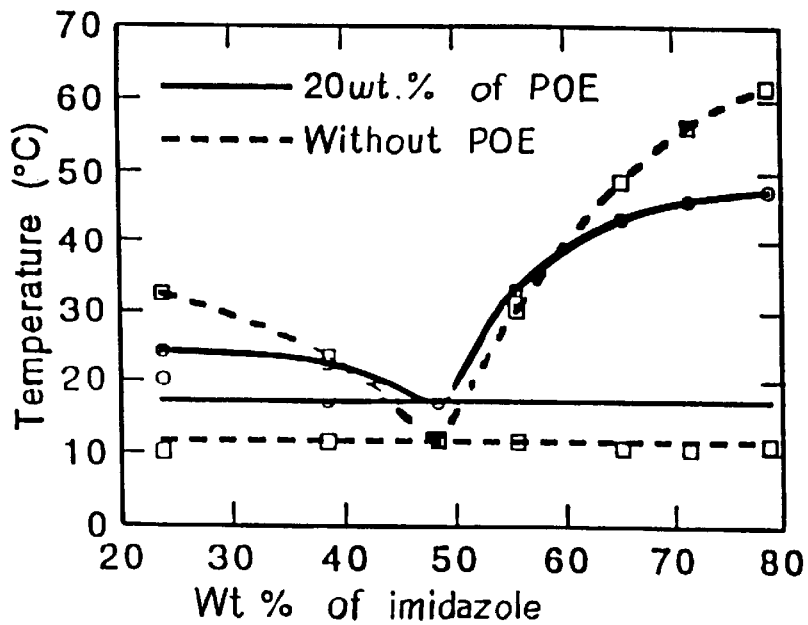
FIG. 5 represents the phase diagrams of the binary mixture imidazole/imidazolium triflate, in the presence and absence of polyethylene oxide or polyethylene glycol.
Figure 6:
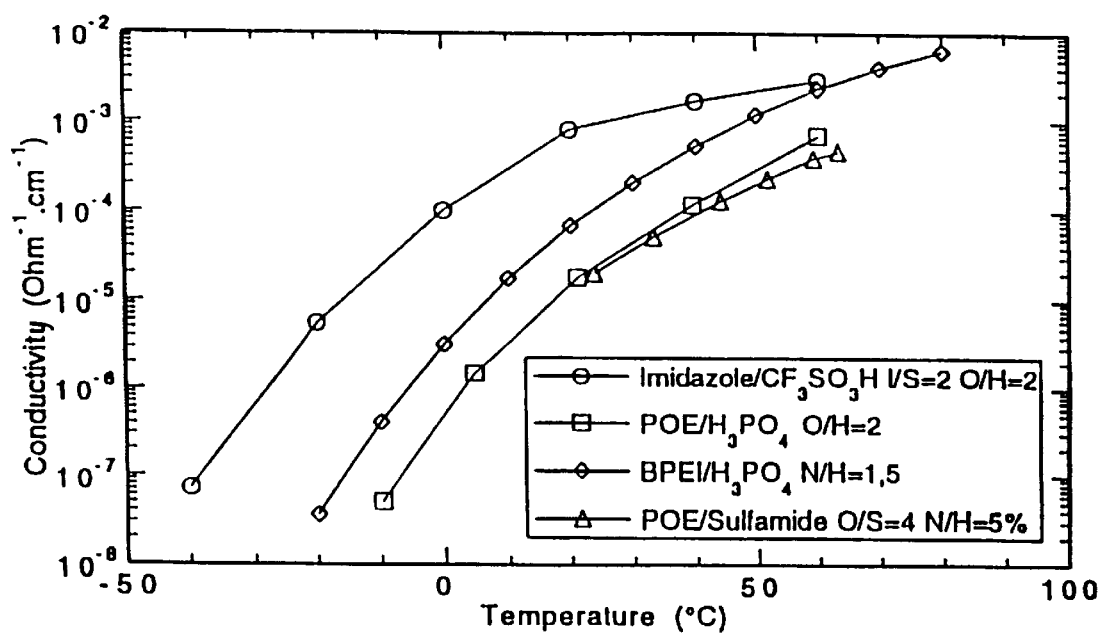
FIG. 6 is a diagram showing the variation of the conductivity of the binary mixture imidazole/imidazolium triflate as a function of the temperature, compared to other electrolytes.

FIG. 5 shows that the addition of 20 wt. % of polyethylene oxide to a binary mixture imidazole/imidazolium triflate having a molar ratio I/S equal to 4 hardly modifies the phase diagram of the system, the system being now in the form a film of polymer electrolyte which is particularly suitable for fabricating thin film electrochemical systems: light-modulating systems such as described above, generators, supercapacitors, sensors, etc. FIG. 6 provides the conductivity of this polymer proton electrolyte and enables one to compare its conductivity which those of other polymer electrolytes which are proton conductors: an electrolyte obtained by mixing orthophosphoric acid and polyethylene oxide ($PEO/H_3PO_4$), an electrolyte obtained by mixing orthophosphoric acid and polyethylene imine ($PHI/H_3PO_4$), an electrolyte obtained by mixing sulfamide and polyethylene oxide (PEO/sulfamide). Therefore, the conductivity of the liquid or polymer electrolytes obtained from the binary mixtures according to the invention can be increased by adding a polar solvent which is hardly volatile, such as dimethylformamide or glymes.

The following non-limiting examples illustrate the invention.

EXAMPLE 1

To a solution in 15 ml of ether of 1.36 g (20 mmoles) of imidazole were added 5.62 g (20 mmoles), of bistrifluoromethanesulfonimide $(CF_3SO_2)_2NH$ (sold by Fluka), the mixture was maintained under agitation for 1 hour and a precipitate was thereafter recovered by filtration on fritted glass having a No. 3 porosity. After drying, the imidazolium salt of bistrifluoromethanesulfonimide of formula:

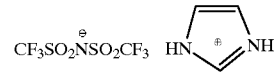

was quantitably recovered.

Crushing in a glove box of a molar mixture of four moles of imidazoles for pool of imidazolium salt enabled one to obtain a liquid conductor having a melting point lower than room temperature. This liquid conductor has a high proton conductivity of about $10^{-3}$ S·cm$^{-1}$ at 20° C.

EXAMPLE 2

In a globe box under argon, a solution in 50 ml of methyl formiate of 6.81 g (100 mmoles) of imidazole, 5.62 g (20 mmoles) of bistrifluoromethanesulfonimide $(CF_3SO_2)_2NH$ (sold by Fluka) and 2.49 g of polyethylene oxide having a mass $M_W=5\times10_6$ (20 wt. % based on the salt) was prepared. This solution was then spreaded on a polypropylene film. After 24 hours in the glove box, a film of transparent polymer electrolyte having good mechanical properties was obtained.

EXAMPLE 3

In a glove box under argon, a thin film electrochemical generator of polymer technology was made utilizing as electrolyte the binary mixture imidazole/imidazolium bistrifluoromethanesulfonimide at its eutectic composition (4:1 molar), by superposing the following layers:

an anode constituted by a mixture of anatase titanium dioxide $TiO_2$ (45 vol. %), Shawinigan black (5 vol. %), the above liquid electrolyte (40 vol. %) and polyethylene oxide having a mass $M_W=3\times10^5$ (10 vol. %) deposited on a current collector of stainless steel;

a cathode constituted by a mixture similar to that of the anode, but substituting for $TiO_2$ manganese dioxide $MnO_2$, previously reduced with an equivalent of hydrazine and deposited on a current collector of stainless steel; and an electrolyte film constituted by a mixture of the above liquid electrolyte (80 wt. %) and polyethylene oxide (20 wt. %).

After assembly the whole was sealed in a button shaped batteries housing. This electrochemical generator initially in a discharge state was cycled between 1.2 V and 500 mV at a charging/discharging rate of C/10. A hundred cycles were thus obtained while maintaining 90% of the capacity at the first discharge. This generator had a useful energy density of about 100 Wh/kg, the energy density calculated by taking into account only electroactive materials being 160 Ah/kg or 709 Ah/l.

An electrochemical generator was also made utilizing the binary mixture imidazoline/imidazolinium bistrifluoromethanesulfonimide at its eutectic composition and gave similar performances.

EXAMPLE 4

In a Warner & Pfilder extruder under argon atmosphere and operating in an anhydrous chamber, polyethylene oxide having a mass $M_W=3\times10^5$ in the form of pellets with a diameter of 2 mm was introduced at one extremity and a mixture of imidazole, 2-hexylimidazolium bistrifluoromethanesulfonimide, hydrogenated iron fluoride $H_xFeF_3$ crushed in grains having a size less than 5 μm, Shawinigan black, KETJENBLACK® K600 (trademark, sold by AKZO) and silica particles (sold under the trademark AEROSIL R974 by Degussa) where introduced into the extruder. The components were introduced in proportions such that $H_xFeF_3$ represents 45% of the total volume, Shawinigan black 3%, KETJENBLACK® K600 1%, the silica particles 1%, the polyethylene oxide 5% and the other components representing 45% of the total volume; the molar ratio imidazole/2-hexylimidazolium bistrifluoromethane sulfonimide being 4 to 1. The whole was extruded at a temperature of 100° C. in the form of a band having a width of 14 cm and a thickness of 120 μm, this cathode film being deposited directly onto a sheet of stainless steel having a thickness of 8 μm.

During the process, the composite cathode film was itself covered with a film of electrolyte having a thickness of 30 μm and obtained by extrusion of a mixture of polyethylene oxide with a mass $M_W=9\times10_5$ (17 wt. %), silica particles (AEROSIL R974) and a mixture of imidazole and 2-hexylimidazolium bistrifluoromethanesulfonimide (80 wt. %, molar ratio 4:1).

During the process, the electrolyte film deposited on the cathode was itself covered with an anode film obtained under the same conditions as the cathode film, but substituting anatase $TiO_2$ for $H_xFeF_3$. The whole was then laminated with a sheet of stainless steel having a thickness of 8 μm.

This electrochemical generator initially in a discharge state was cycled between 1.2 V and 500 mV at a charging/discharging rate of C/10. One thousand cycles were thus obtained while maintaining 78% of the capacity at the first discharge.

EXAMPLE 5

An electrochemical generator similar to that described in Example 3 was made, but utilizing on the one hand organic electroactive materials, either an anthrahydroquinone (oxanthranol)-based anode and a tetrachlorohydrotuinone (chloranil)- based cathode and, on the other hand, a binary mixture triazole/bisfluorosulfononimide, at its eutectic composition and gelled with polyvinylidene fluoride (sold by Montedison) instead of polyethylene oxide.

Figure 7:
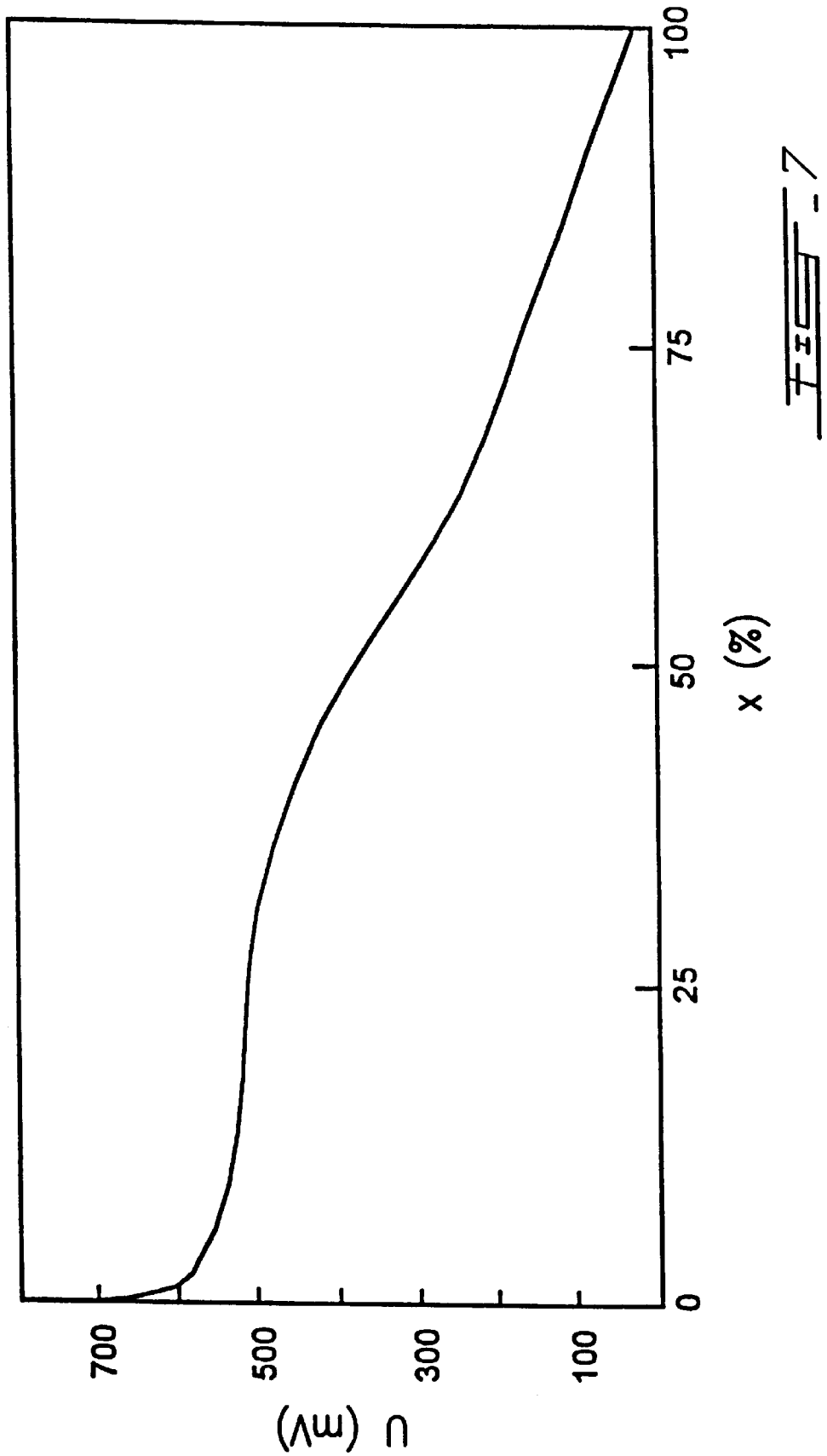
FIG. 7 represents the discharge curve obtained with an electrochemical generator comprising a binary mixture triazole/triazolium bisfluoro-sulfonimide.

The discharge curve obtained at a discharging rate of C/30 is shown in FIG. 7. In this figure, the voltage of generator, U, expressed in mV is given in ordinate, and the rate of use of the electroactive materials, x, expressed in % is given in abscissa.

This generator has an energy density of 120 Ah/kg calculated by taking into account only the electroactive materials.

EXAMPLE 6

An electrochemical supercapacitor was made utilizing ruthenium dioxide $RuO_2$-based electrode. This type of supercapacitor takes advantage of the phenomenon of pseudo-insertion of the proton in these oxides. The electrodes were obtained by vacuum deposition. The supercapacitor was assembled utilizing two of these electrodes and an electrolyte constituted of the binary mixture 1,3,4-triazole/1,3,4-triazolium trisfluoro-sulfonylmethylide at its eutectic composition.

This supercapacitor was cycled between 0 and 1 V at a charging/discharging rate of 10 C. More than 300000 cycles were effected under these conditions, the capacity at the 300000th cycle still being equal to 70% of the capacity of the first cycle. This supercapacitor has an energy density greater than 5 Wh/kg and can furnish a power greater than 1 kW/kg.

EXAMPLE 7

An electrochemical supercapacitor was made utilizing activated carbon-based electrodes. These electrodes were composites obtained from carbon fiber and aluminum fiber in a reducing medium. The electrodes having a thickness of 150 μm were placed on either side of a microporous polyethylene having a thickness of 40 μm, the whole was impregnated with the binary mixture pyrazole/pyrazolium bis(trifluoromethanesulfonyl) methide at its eutectic composition, then sealed in a button-shaped battery housing, in a glove box. Good performances were obtained with this super-capacitor, and more than 200000 cycles of charging/discharging between 0 and 1 with an energy density greater than 10 Wh/l and a delivered power greater than 1500 W/l were effected.

EXAMPLE 8

An electrochrome system was made in a glove box under argon, utilizing as electrolyte the binary mixture 1,2,3-triazole/1,2,3-triazolium bistrifluoromethanesulfonimide at its eutectic composition (molar ratio 4:1), by superposing the following layers:

a transparent electrode obtained by depositing on a glass plate a layer of hydrogenated iridium oxide $H_xIrO_2$ and a conducting underlayer of tin oxide;

a film of transparent polymer electrolyte constituted of a mixture of the above liquid electrolyte (80 wt. %) and polyethylene oxide (20 wt. %); and a transparent electrode constituted of a layer of tungsten trioxide $WO_3$ and a conducting underlayer of tin oxide.

This electrochrome enabled one to obtain a variation of the optical absorption from 80% in the discolored state to 30% in the colored state.

Figure 8:
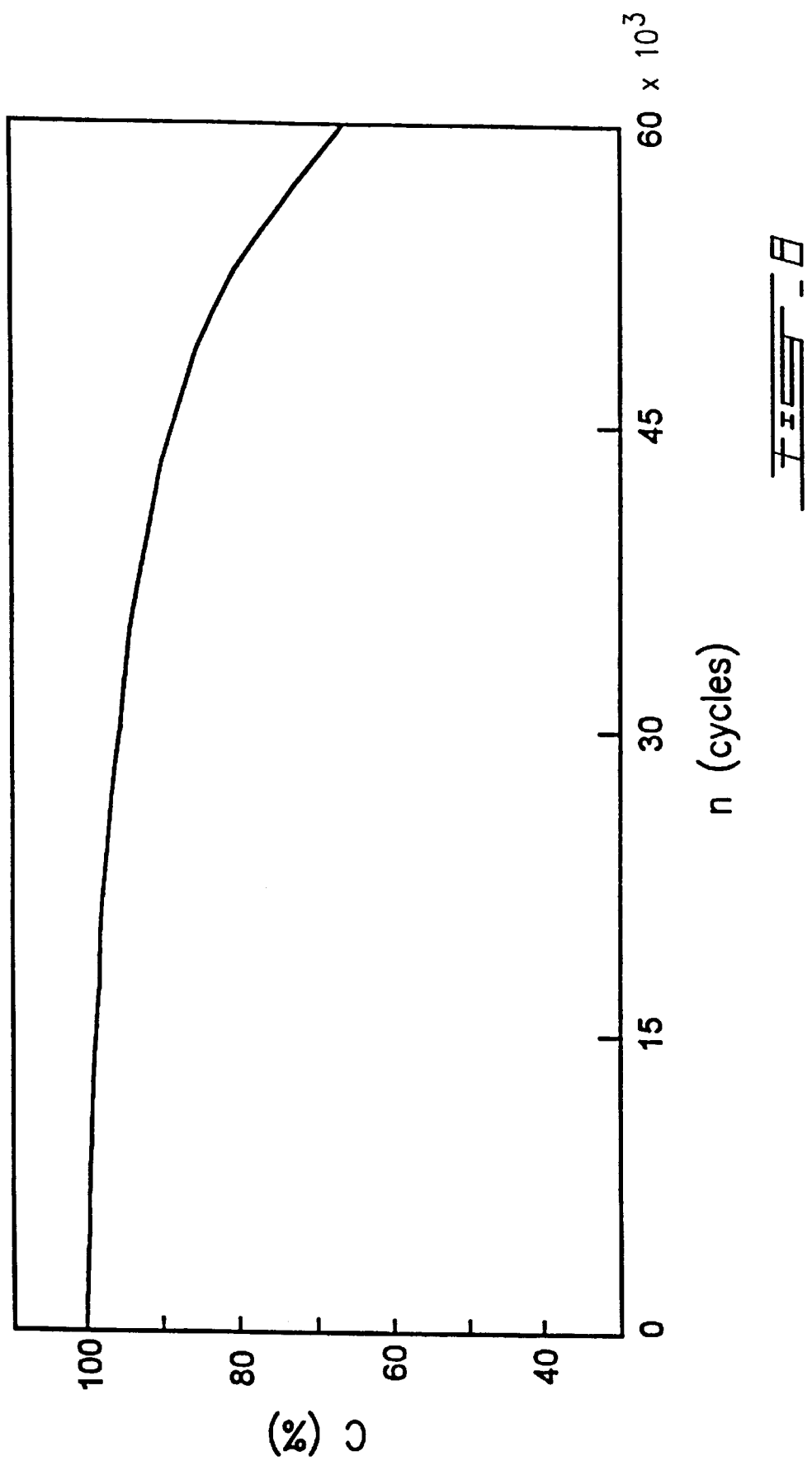
FIG. 8 represents the cycling curve obtained with an electrochrome system comprising a polymer electrolyte formed of the binary mixture 1,2,3-triazole/1,2,3-triazolium bis (trifluoromethanesulfonimide) dissolved in polyethylene oxide.

The cycling curve obtained with the above electrode at a charging/discharging rate of 10 C. is shown in FIG. 8. In this figure, the coulombic capacitance relative to that of the first cycle, C, expressed in percentage is given in ordinate, and the number of cycles, n, expressed in thousands of cycles is given in abscissa.

EXAMPLE 9

An electrochrome was made by dissolving two complementary coloring agents in the binary mixture imidazole/imidazolium bistrifluoromethanesulfonimide at its eutectic composition. In a glove box, 1.75 g (5 mmoles) of imidazolium bistrifluoromethanesulfonimide and 1.36 g (20 mmoles) of imidazole were crushed together. Afterwards, to the binary mixture were added 16.5 mg (50 µmoles) of leuco(malachite green), in the reduced state which is colorless, and 30.8 mg (50 µmoles) of 3-(4,5-dimethylthiazolyl-2-yl)-2,5-diphenyl-2H-tetrazolium (MTT) bistrifluoromethanesulfonimide, in the oxidized state which is colorless (obtained by anionic exchange in water from the bromide). 8 wt. % of silica particles (AEROSIL R 974) were then added. The viscous liquid obtained was deposited between two glass plates covered with a conductive layer of tin indium oxide (ITO). After having sealed the assembly to render it airtight, a voltage of 1300 mV was applied to the exterior with a potentiostat. The system then became colored, the oxidized form of the leuco(green malachite) and the reduced form of the MTT each exhibiting an intense absorption band in the visible spectrum. By applying a voltage of −500 mV, a relatively rapid discoloration of the system (less than 60 s) was observed. Such an electrochrome system has a long life and is easy to use, even in the case of systems having a large size (greater than m$^2$) which utilize glass as well as a suitably treated polymer as transparent conducting electrode. Moreover, the energy necessary for maintaining the coloration is relatively low, less than 1 W/m$^2$.

EXAMPLE 10

An electrochrome system similar to that described in Example 9 was made, but utilizing as coloring agents N,N,N',N'-tetramethylphenylenediamine (colorless reduced state) and dimethylviologen bistrifluoromethanesulfonimide (colorless oxidized state). This electrochrome system also becomes colored when applying a voltage to the two electrodes. Surprisingly, this system exhibits an important stability despite the radical mechanism involved during the coloration. The liquid electrolyte, in addition to solubilizing the coloring agents, enables the radicals to be stabilized.

EXAMPLE 11

An electrochemical supercapacitor was made utilizing the binary mixture triazole/triazolebistrifluoromethanesulfonimide and ruthenium oxide RuO2.

EXAMPLE 12

An electrochemical supercapacitor was made utilizing the binary mixture imidazolium/imidazolium-tris(fluorosulfonyl)methide and activated carbon oxide electrodes, and adding a glyme as plastifying agent.

EXAMPLE 13

An electrochrome system H$_x$IrO2/WO3 was made utilizing the binary mixture triazole/triazolium triflate to which was added polyethylene oxide diacrylate and a sensitizing agent (Irgacure) and crosslinking the whole under U.V. radiation.

EXAMPLE 14

An electrochrome with dyes was made utilizing two complementary dyes dissolved in a salt of tristrifluoromethanesulfonylmethide.

We claim:

1. A proton conductor in liquid form, comprising a mixture of the following components (a) and (b):

a) an acid addition salt of a nitrogen base, having the formula:

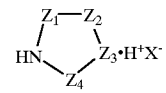

wherein:

$Z_1$, $Z_2$, $Z_3$ and $Z_4$, identical or different, each represent a group —N= or —C(Y$_i$)= in which Y$_i$ represents a hydrogen atom, a linear or branched alkyl group having 1 to 20 carbon atoms, a fluoroalkyl radical having 1 to 20 carbon atoms, or an oxoalkyl or azaalkyl radical having 1 to 20 carbon atoms, with the proviso that at least one and at most two of the groups $Z_1$, $Z_2$, $Z_3$ and $Z_4$ represents —N=, two adjacent carbon atoms being optionally hydrogenated and the nitrogen base optionally being part of a polymeric network, and X$^-$ represents an anion derived from an acid selected from the group consisting of sulfonic acids of formula R$_F$SO$_3$H, sulfonimides of formula (R$_F$SO$_2$)(R'$_F$SO$_2$)NH and methylides of formula (R$_F$SO$_2$)(R'$_F$SO$_2$)CH$_2$ or (R$_F$SO$_2$) (R'$_F$SO$_2$) (R"$_F$SO$_2$) in which R$_F$, R'$_F$ and R"$_F$ each represents a radical F(CF$_2$)$_n$—, n being comprised between 0 and 6, the acid optionally being part of a polymeric network; and b) a nitrogen base having the formula:

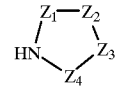

in which $Z_1$, $Z_2$, $Z_3$ and $Z_4$ have the aforesaid meanings, the nitrogen base optionally being part of a polymeric network; and wherein components (a) and (b) are present in proportions to form a composition having a melting point lower than 25° C.

2. A proton conductor according to claim 1, wherein the composition comprising the mixture of components (a) and (b) is substantially eutectic.

3. A proton conductor according to claim 1, wherein component (a) is an acid addition salt of a nitrogen base consisting of an imidazole having the formula:

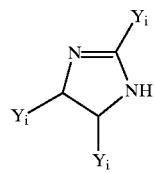

wherein $Y_i$ represents a hydrogen atom, a linear or branched alkyl group having 1 to 20 carbon atoms, a fluoroalkyl radical having 1 to 20 carbon atoms, or an oxoalkyl or azaalkyl radical having 1 to 20 carbon atoms.

4. A proton conductor according to in claim 1, wherein component (a) is an acid addition salt of a nitrogen base consisting of a 1,2,3-triazole having the formula:

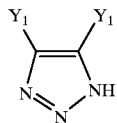

wherein $Y_i$ represents a hydrogen atom, a linear or branched alkyl group having 1 to 20 carbon atoms, a fluoroalkyl radical having 1 to 20 carbon atoms, or an oxoalkyl or azaalkyl radical having 1 to 20 carbon atoms.

5. A proton conductor according to claim 1, wherein component (a) is an acid addition salt of a nitrogen base consisting of a 1,3,4-triazole having the formula:

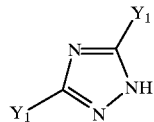

wherein $Y_i$ represents a hydrogen atom, a linear or branched alkyl group having 1 to 20 carbon atoms, a fluoroalkyl radical having 1 to 20 carbon atoms, or an oxoalkyl or azaalkyl radical having 1 to 20 carbon atoms.

6. A proton conductor according to claim 1, wherein component (a) is an acid addition salt of a base consisting of a pyrazole having the formula:

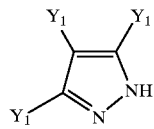

wherein $Y_i$ represents a hydrogen atom, a linear or branched alkyl group having 1 to 20 carbon atoms, a fluoroalkyl radical having 1 to 20 carbon atoms, or an oxoalkyl or azaalkyl radical having 1 to 20 carbon atoms.

7. A proton conductor according to claim 1, wherein component (a) is an acid addition salt of a nitrogen base consisting of an imidazoline having the formula:

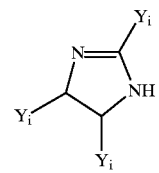

wherein $Y_i$ represents a hydrogen atom, a linear or branched alkyl group having 1 to 20 carbon atoms, a fluoroalkyl radical having 1 to 20 carbon atoms, or an oxoalkyl or azaalkyl radical having 1 to 20 carbon atoms.

8. A proton conductor according to claim 1, wherein the acid is selected from the group consisting of triflic acid, bisfluorosulfonimide, bistrifluoromethanesulfonimide, bistrifluoromethanesulfonylmethane, tristrifluoromethanesulfonylmethane and trisfluorosulfonylmethane.

9. A proton conductor according to claim 3, wherein component (a) is an addition salt of imidazole with triflic acid.

10. A proton conductor according to claim 3, wherein component (a) is an addition salt of imidazole with bisfluorosulfonimide.

11. A proton conductor according to claim 3, wherein component (a) is an addition salt of imidazole with bistrifluoromethanesulfonimide.

12. A proton conductor according to claim 3, wherein component (a) is an addition salt of 2-hexylimidazole with triflic acid.

13. A proton conductor according to claim 1, wherein component (b) is a nitrogen base consisting of an imidazole having the formula:

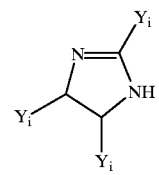

wherein $Y_i$ represents a hydrogen atom, a linear or branched alkyl group having 1 to 20 carbon atoms, a fluoroalkyl radical having 1 to 20 carbon atoms, or an oxoalkyl or azaalkyl radical having 1 to 20 carbon atoms.

14. A proton conductor according to claim 1, wherein component (b) is a nitrogen base consisting of a 1,2,3-triazole having the formula:

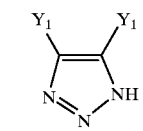

wherein $Y_i$ represents a hydrogen atom, a linear or branched alkyl group having 1 to 20 carbon atoms, a fluoroalkyl radical having 1 to 20 carbon atoms, or an oxoalkyl or azaalkyl radical having 1 to 20 carbon atoms.

15. A proton conductor according to claim 1, wherein component (b) is a nitrogen base consisting of a 1,3,4-triazole having the formula:

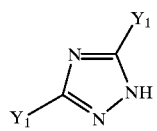

wherein $Y_i$ represents a hydrogen atom, a linear or branched alkyl group having 1 to 20 carbon atoms, a fluoroalkyl radical having 1 to 20 carbon atoms, or an oxoalkyl or azaalkyl radical having 1 to 20 carbon atoms.

16. A proton conductor according to claim 1, wherein component (b) is a nitrogen base consisting of a pyrazole having the formula:

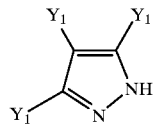

wherein $Y_i$ represents a hydrogen atom, a linear or branched alkyl group having 1 to 20 carbon atoms, a fluoroalkyl radical having 1 to 20 carbon atoms, or an oxoalkyl or azaalkyl radical having 1 to 20 carbon atoms.

17. A proton conductor according to claim 1, wherein component (b) is a nitrogen base consisting of an imidazoline having the formula:

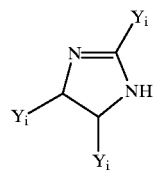

wherein $Y_i$ has the aforesaid meaning.

18. A proton conductor according to claim 1, wherein component (b) is a nitrogen base consisting of imidazole.

19. A proton conductor according to claim 1, wherein component (b) is a nitrogen base consisting of 2-hexylimidazole.

20. A proton conductor according to claim 1, comprising a mixture of 3 moles of imidazole and one mole of imidazolium triflate.

21. A proton conductor according to claim 1, comprising a mixture of 4 moles of imidazole and one mole of imidazolium bis(trifluoromethanesulfonimide).

22. A proton conductor according to claim 1, comprising a mixture of 4 moles of imidazole and one mole of imidazolium bisfluorosulfonimide.

23. A proton conductor according to claim 1, comprising a mixture of 3 or 4 moles of 2-hexylimidazole and one mole of 2-hexylimidazolium.

24. A liquid electrolyte consisting of a proton conductor as defined in claim 1.

25. A polymer electrolyte comprising a proton conductor as defined in claim 1, dissolved in a polymer comprising at least one polar group.

26. A polymer electrolyte according to claim 25, wherein the polymer is polyethylene oxide.

27. An electrochrome system comprising two transparent semi-conducting electrodes arranged in spaced-apart opposed relationship to one another, each of said electrodes being fixed on one side thereof to a transparent support and comprising on an other side thereof a coating of a wide band gap semi-conducting material, and a polymer electrolyte as defined in claim 25, disposed between said electrodes and contacting the coatings of semi-conducting material.

28. An electrochrome system comprising two transparent semi-conducting electrodes arranged in spaced-apart opposed relationship to one another, each of said electrodes being fixed on one side thereof to a transparent support, and a polymer electrode as defined in claim 25, disposed between said electrodes and contacting the other side of each electrode, said polymer electrolyte comprising at least one redox coloring agent added thereto.

29. An electrochrome system comprising two transparent semi-conducting electrodes arranged in spaced-apart opposed relationship to one another, each of said electrodes being fixed on one side thereof to a transparent support and one of said electrodes comprising on an other side thereof a coating of a wide band gap semi-conducting material, and a polymer electrolyte as defined in claim 25, disposed between said electrodes and contacting the coating of semi-conducting material, said polymer electrolyte comprising at least one redox couple added thereto, said redox couple being complementary to said wide band gap semi-conducting material.

30. An electrochrome generator comprising an anode, a cathode and an electrolyte as defined in anyone of claim 24, disposed between said anode and s aid cathode.

31. An electrochemical supercapacitor comprising an anode, a cathode and an electrolyte as defined in claim 24, disposed between said anode and said cathode.

32. A sensor comprising a proton conductor as defined in claim 1.

33. An anhydrous protic solvent consisting of a proton conductor as defined in claim 1.

34. Use of an anhydrous protic solvent as defined in claim 33, for carrying out chemical, photochemical or electrochemical reactions.

* * * * *